United States Patent
Nishida et al.

(10) Patent No.: US 10,910,186 B2
(45) Date of Patent: Feb. 2, 2021

(54) ION GENERATION DEVICE WITH BRUSH-LIKE DISCHARGE ELECTRODES

(71) Applicant: SHARP KABUSHIKI KAISHA, Sakai (JP)

(72) Inventors: Hiromu Nishida, Sakai (JP); Yoshinori Sekoguchi, Sakai (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 220 days.

(21) Appl. No.: 15/552,480

(22) PCT Filed: Feb. 9, 2016

(86) PCT No.: PCT/JP2016/053830
§ 371 (c)(1),
(2) Date: Aug. 21, 2017

(87) PCT Pub. No.: WO2017/022255
PCT Pub. Date: Feb. 9, 2017

(65) Prior Publication Data
US 2018/0053620 A1 Feb. 22, 2018

(30) Foreign Application Priority Data
Aug. 5, 2015 (JP) .................. 2015-155555

(51) Int. Cl.
*H01J 27/26* (2006.01)
*A61L 9/22* (2006.01)
(Continued)

(52) U.S. Cl.
CPC ............... *H01J 27/26* (2013.01); *A61L 9/22* (2013.01); *B60H 3/0071* (2013.01); *H01J 27/22* (2013.01);
(Continued)

(58) Field of Classification Search
CPC .......... A61L 9/22; B03C 3/40; B60H 3/0071; B65H 2301/5133; C02F 1/4608;
(Continued)

(56) References Cited

U.S. PATENT DOCUMENTS 4,734,580 A * 3/1988 Rodrigo ............... H01T 23/00
250/324
5,958,165 A * 9/1999 Takeuchi ............. B32B 18/00
156/89.11
(Continued)

FOREIGN PATENT DOCUMENTS

CN 201478694 U 5/2010
CN 204165142 U * 2/2015
(Continued)

OTHER PUBLICATIONS

Co-pending letter.
(Continued)

*Primary Examiner* — Jared Fureman
*Assistant Examiner* — Nicolas Bellido
(74) *Attorney, Agent, or Firm* — ScienBiziP, P.C.

(57) ABSTRACT

An ion generating device (1) includes: a discharge electrode (21,22), protruding from a surface of the ion generating device, for generating ions by electric discharge, the discharge electrode having (i) a tip part (31) including a brush-like electrically conductive member and (ii) a base end part (33) to which the brush-like electrically conductive member is attached, and the base end part protruding from the surface of the ion generating device for a length (L2) that is longer than a length (L1) of the tip part.

7 Claims, 6 Drawing Sheets

(51) Int. Cl.
*B60H 3/00* (2006.01)
*H01J 27/22* (2006.01)
*H01T 19/04* (2006.01)
*H01T 23/00* (2006.01)
*H01T 19/02* (2006.01)
*F24F 3/16* (2006.01)

(52) U.S. Cl.
CPC ............. *H01T 19/02* (2013.01); *H01T 19/04* (2013.01); *H01T 23/00* (2013.01); *F24F 2003/1682* (2013.01)

(58) Field of Classification Search
CPC .... F24F 2003/1682; H01J 27/02; H01J 27/22; H01J 27/26; H01J 37/08; H01L 27/26; H01T 19/02; H01T 19/04; H01T 23/00; H05H 2001/481; Y10T 29/49002
USPC .......................................... 361/231; 313/230
See application file for complete search history.

(56) References Cited

U.S. PATENT DOCUMENTS

| | | | |
|---|---|---|---|
| 6,653,638 B2 | 11/2003 | Fujii | |
| 8,559,157 B2* | 10/2013 | Nishida | H01T 23/00 361/230 |
| 9,025,303 B2* | 5/2015 | Waddell | A61L 9/22 361/231 |
| 9,441,845 B2* | 9/2016 | Waddell | B03C 3/04 |
| 2006/0214111 A1* | 9/2006 | Luo | H01T 23/00 250/423 R |
| 2009/0042502 A1* | 2/2009 | Kim | B60H 3/0071 454/139 |
| 2010/0175391 A1* | 7/2010 | Jee | B60H 3/0071 62/3.1 |
| 2011/0250475 A1* | 10/2011 | Yamamoto | H01M 2/0277 429/7 |
| 2012/0326197 A1* | 12/2012 | Ohbayashi | C09K 11/025 257/98 |
| 2013/0120895 A1 | 5/2013 | Lai | |
| 2013/0146781 A1* | 6/2013 | Sekoguchi | H01T 23/00 250/423 R |
| 2013/0214173 A1* | 8/2013 | Noda | H01J 27/022 250/423 R |
| 2014/0103793 A1* | 4/2014 | Nishida | H01T 23/00 313/231.71 |
| 2016/0104595 A1* | 4/2016 | Nishida | H01T 19/04 313/230 |
| 2016/0204581 A1* | 7/2016 | Nishida | B03C 3/38 250/423 F |
| 2016/0218490 A1* | 7/2016 | Nishida | A61L 9/22 |
| 2018/0053620 A1* | 2/2018 | Nishida | A61L 9/22 |
| 2018/0053621 A1* | 2/2018 | Nishida | A61L 9/22 |

FOREIGN PATENT DOCUMENTS

| | | | |
|---|---|---|---|
| CN | 105493361 A | | 4/2016 |
| EP | 0048102 A1 | | 3/1982 |
| JP | H08-112549 A | | 5/1996 |
| JP | H10-074576 A | | 3/1998 |
| JP | H11-168276 A | | 6/1999 |
| JP | 2000340393 A | * | 12/2000 |
| JP | 3089869 U | | 11/2002 |
| JP | 2003-229232 A | | 8/2003 |
| JP | 3112435 U | | 8/2005 |
| JP | 2008-34220 A | | 2/2008 |
| JP | 2008-101818 A | | 5/2008 |
| JP | 2008-112714 A | | 5/2008 |
| JP | 2009238602 A | * | 10/2009 |
| JP | 2012-038510 A | | 2/2012 |
| JP | 3174998 U | | 4/2012 |
| JP | 2014032783 A | * | 2/2014 |
| JP | 2015-5387 A | | 1/2015 |
| JP | 2017021982 A | * | 1/2017 ............... A61L 9/22 |
| KR | 20-0429549 Y1 | | 10/2006 |
| WO | WO-2014185682 A1 | * | 11/2014 ............... F24F 13/20 |
| WO | 2015-050045 A1 | | 4/2015 |

OTHER PUBLICATIONS

Office Action dated Jun. 27, 2019 in U.S. Appl. No. 15/552,482.
Final Office Action dated Oct. 7, 2019 for U.S. Appl. No. 15/552,482.
Non-Final Office Action dated Mar. 3, 2020 for U.S. Appl. No. 15/552,482.

* cited by examiner

ION GENERATION DEVICE WITH BRUSH-LIKE DISCHARGE ELECTRODES

TECHNICAL FIELD

The present invention relates to an ion generating device and an electrical apparatus including the ion generating device.

BACKGROUND ART

An ion generating device has been conventionally used for, for example, indoor air cleaning, sterilization, or deodorization.

An ion generating device generally includes a discharge electrode for generating ions by electric discharge. An ion generating device generates ions by, for example, causing corona discharge to occur between (a) a tip of a discharge electrode to which a high voltage is applied and (b) an induction electrode.

As a discharge electrode for generating ions by thus applying thereto a high voltage, a brush-like discharge electrode including a plurality of fibrous electrically conductive members having bundled roots is known.

For example, Patent Literature 1 discloses a brush-like discharge electrode that is arranged such that while a bundle of carbon fibers partially extends out from one end of a metallic pipe by a given length, the metallic pipe is pressure-fixed to the other end of the bundle of carbon fibers.

CITATION LIST

Patent Literature

[Patent Literature 1]
Japanese Patent Application Publication, Tokukai, No. 2003-229232 (Publication Date: Aug. 15, 2003)

SUMMARY OF INVENTION

Technical Problem

According to such a brush-like discharge electrode to which a high voltage is applied, electrically conductive members on a side thereof which serves as a tip side of the electrically conductive members and on which the electrically conductive members are not bundled electrically repel each other and spread. Thus, use of such a brush-like discharge electrode causes a further increase in amount of generation of ions than use of, for example, a needle-like discharge electrode in a case where an identical voltage is applied to each of the brush-like discharge electrode and the needle-like discharge electrode. This results in achievement of favorable ion release.

Note, however, that in a case where a tip of the bundle of carbon fibers spreads, the carbon fibers may contact a surface of an ion generating device. In this case, since a high voltage is applied to the carbon fibers, abnormal electric discharge may occur in the surface of the ion generating device by the carbon fibers, so that ions may be generated in a lower amount.

The present invention has been made in view of the problems, and an object of the present invention is to provide, for example, an ion generating device that makes it possible to prevent a plurality of linear electrically conductive members provided in a discharge electrode from contacting a surface of the ion generating device.

Solution to Problem

In order to attain the object, an ion generating device in accordance with an embodiment of the present invention includes: a discharge electrode, protruding from a surface of the ion generating device, for generating ions by electric discharge, the discharge electrode having (i) a tip part including a plurality of linear electrically conductive members and (ii) a base end part to which the plurality of electrically conductive members is attached, and the base end part protruding from the surface for a length that is longer than a length of the tip part.

In order to attain the object, an electrical apparatus in accordance with an embodiment of the present invention includes: an ion generating device mentioned above.

Advantageous Effects of Invention

An embodiment of the present invention makes it possible to provide (i) an ion generating device that makes it possible to prevent a plurality of linear electrically conductive members provided in a discharge electrode from contacting a surface of the ion generating device and (ii) an electrical apparatus including the ion generating device.

DESCRIPTION OF EMBODIMENTS

Figure 1:
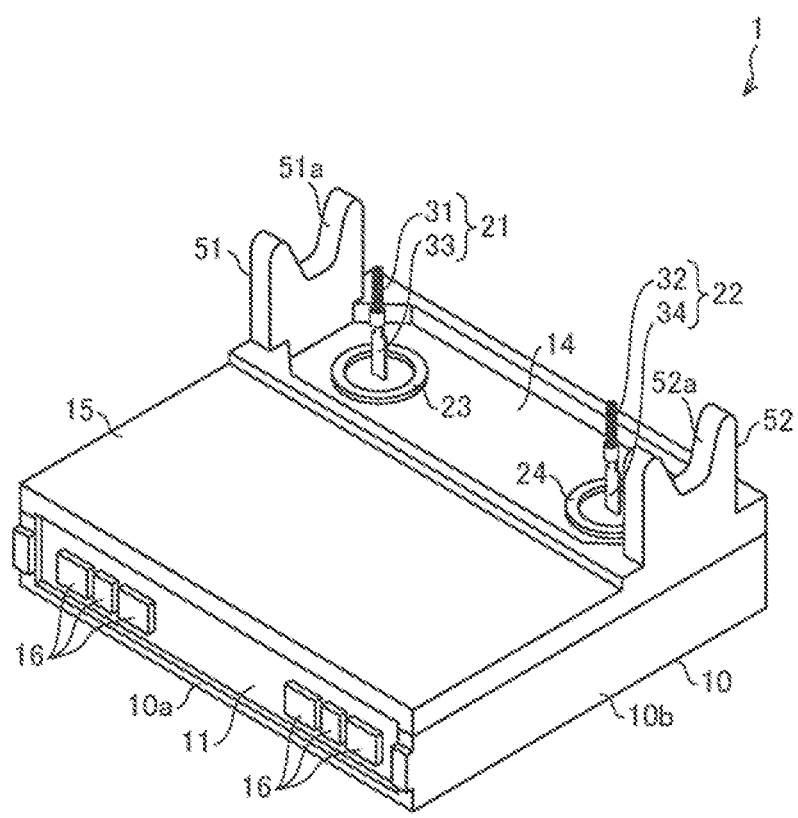
FIG. 1 is a perspective view schematically illustrating an arrangement of an ion generating device in accordance with Embodiment 1 of the present invention.

Embodiments of the present invention are specifically described below. Note that for convenience, members having functions identical to those of the respective members described in the embodiments are given respective identical reference numerals, and a description of those members is omitted as appropriate.

Embodiment 1

First, an embodiment of the present invention is described with reference to FIG. 1 through FIG. 3.

FIG. 1 is a perspective view schematically illustrating an arrangement of an ion generating device in accordance with Embodiment 1. FIG. 2 is a front view, a plan view, and a side view each schematically illustrating the arrangement of the ion generating device.

Figure 2:
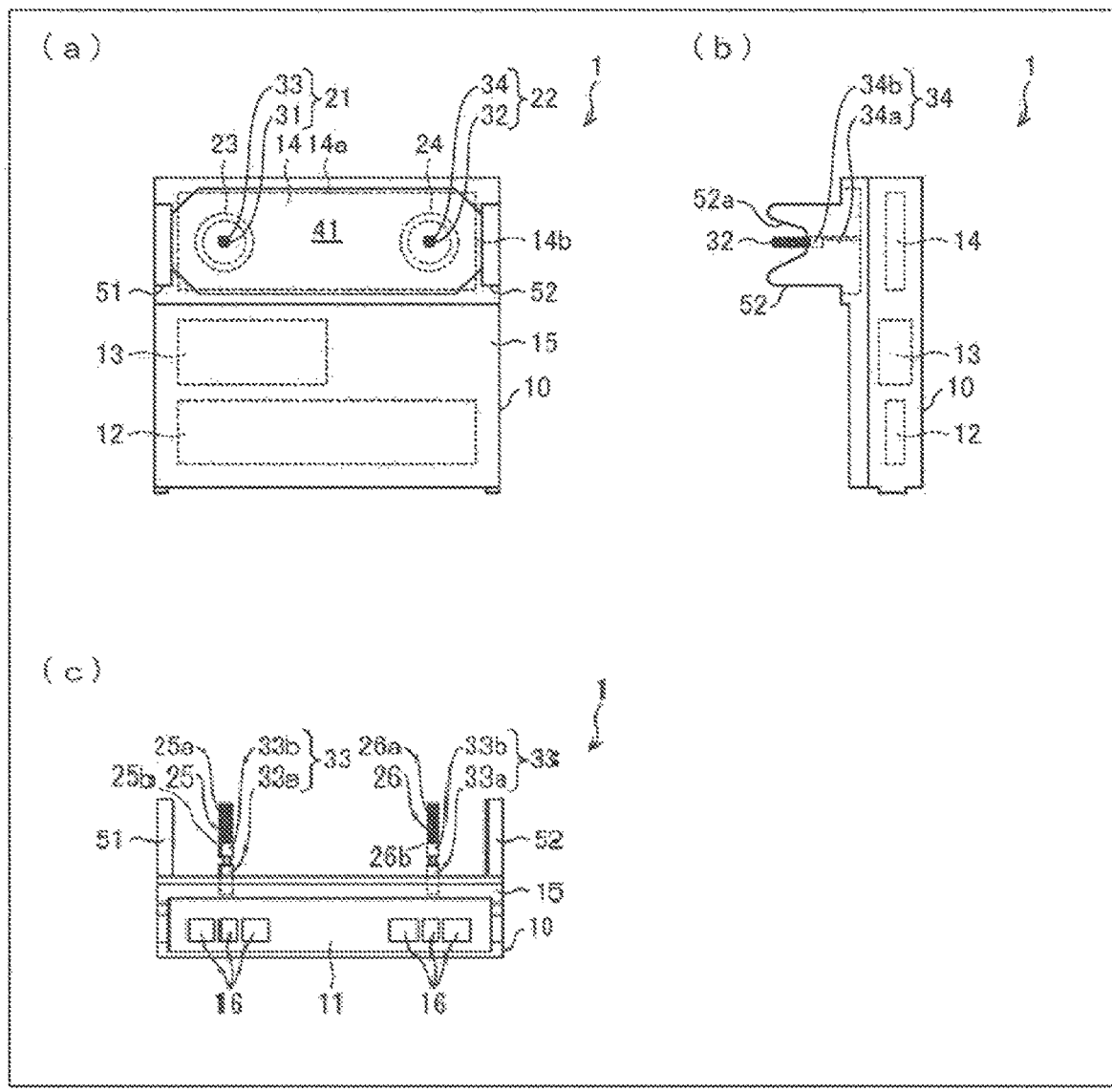
FIGS. 2a-2c are, respectively, a plan view, a side view, and a front view each schematically illustrating the arrangement of the ion generating device in accordance with Embodiment 1 of the present invention.

As illustrated in FIG. 1 and FIG. 2, an ion generating device 1 of Embodiment 1 includes a case 10 (housing), which is quadrangular, a substrate 12 for a transformer drive circuit (hereinafter referred to as a "transformer drive circuit substrate 12"), a high voltage transformer 13 (high voltage circuit), a substrate 14 for an ion generating element (hereinafter referred to as an "ion generating element substrate 14"), a lid 15, discharge electrodes 21 and 22, and protective plates 51 and 52 (protruding members).

The case 10 is box-shaped, has a front surface and an upper surface, each of which is open, and is made of an insulating resin. The case 10 has a front part that is provided with a substrate 11 for external connection (hereinafter referred to as an "external connection substrate 11"). The case 10 contains therein the transformer drive circuit substrate 12, the high voltage transformer 13, and the ion generating element substrate 14, which are arranged in this order from the front side. The case 10 has an upper surface to which the lid 15 is provided so as to cover the external connection substrate 11, the transformer drive circuit substrate 12, and the high voltage transformer 13.

The external connection substrate 11 has a surface that is provided with a plurality of (e.g., six) connection terminals 16. Each of the plurality of connection terminals 16 is made of an electrically conductive film provided on the surface of the external connection substrate 11 and is formed by, for example, print patterning, plating, sputtering, or chemical vapor deposition (CVD). The electrically conductive film is made of a material such as copper (Cu), aluminum (Al), gold (Au), or an alloy of copper (Cu), aluminum (Al), and gold (Au), and has a thickness of an order of several ten μm (e.g., a thickness of 35 μm). The connection terminals 16 are provided so as to be exposed on an outside of the case 10 while the external connection substrate 11 is being supported by the case 10.

The transformer drive circuit substrate 12 is provided with a high voltage transformer drive circuit. The high voltage transformer drive circuit is directed to drive the high voltage transformer 13 by an externally inputted voltage.

The high voltage transformer 13 is directed to be driven by the high voltage transformer drive circuit so as to raise a voltage supplied thereto. The ion generating element substrate 14 is provided with an ion generating element. The ion generating element is directed to generate at least either of positive ions and negative ions in response to application thereto the voltage raised by the high voltage transformer 13.

The ion generating element includes discharge electrodes 21 and 22 and induction electrodes 23 and 24, which are circular. The discharge electrode 21 is provided to one side part of the ion generating element substrate 14, and the induction electrode 23 is provided around a place where the discharge electrode 21 is provided. The discharge electrode 22 is provided to the other side part of the ion generating element substrate 14, and the induction electrode 24 is provided around a place where the discharge electrode 22 is provided.

The induction electrode 23 is an electrode for forming an electric field between the induction electrode 23 and the discharge electrode 21, and the induction electrode 24 is an electrode for forming an electric field between the induction electrode 24 and the discharge electrode 22. The discharge electrode 21 is an electrode for generating negative ions between the discharge electrode 21 and the induction electrode 23, whereas the discharge electrode 22 is an electrode for generating positive ions between the discharge electrode 22 and the induction electrode 24. Note that the induction electrodes 23 and 24 each have ground electric potential.

The ion generating element substrate 14 has a surface that is covered with an insulating sealing member 41 whose surface, for example, substantially do not differ in level from a surface of the lid 15 (see FIG. 2). As the insulating sealing member 41, an insulating material such as an epoxy resin or an urethane resin is used.

The discharge electrodes 21 and 22, which are provided so as to perpendicularly extend from the surface of the ion generating element substrate 14, protrude from the surface of the insulating sealing member 41.

The discharge electrode 21 is a brush-like discharge electrode including a plurality of linear electrically conductive members 25. The discharge electrode 21 has a tip part 31 formed like a brush; and a base end part 33 to which the plurality of linear electrically conductive members 25 is attached. The discharge electrode 22 is a brush-like discharge electrode including a plurality of linear electrically conductive members 26. The discharge electrode 22 has a tip part 32 formed like a brush; and a base end part 34 to which the plurality of electrically conductive members 26 is attached.

Note that the tip parts 31 and 32 refer to parts located ahead of the respective base end parts 33 and 34. Specifically, the tip part 31 refers to a part that extends from a respective plurality of tips 25a of the plurality of electrically conductive members 25, which is a brush-like bundle, to a connection end (contact end) 25b of the plurality of electrically conductive members 25 at which the connection end (contact end) 25b of the plurality of electrically conductive members 25 is in connection (in contact) with the base end part 33. The tip part 32 refers to a part that extends from a respective plurality of tips 26a of the plurality of electrically conductive members 26, which is a brush-like bundle, to a connection end (contact end) 26b of the plurality of electrically conductive members 26 at which the connection end (contact end) 26b of the plurality of electrically conductive members 26 is in connection (in contact) with the base end part 34. Examples of the term "linear" include terms such as "thready", "fibrous", and "wiry".

The tip parts 31 and 32 of the discharge electrodes 21 and 22 are made of an electrically conductive member such as metal, carbon fiber, electrically conductive fiber, or electrically conductive resin. The plurality of electrically conductive members 25 of the tip part 31 and the plurality of electrically conductive members 26 of the tip part 32 each have an outside diameter of not less than 5 μm and not more than 30 μm. In a case where the plurality of electrically conductive members 25 and the plurality of electrically conductive members 26 each have an outside diameter of not less than 5 μm, the plurality of electrically conductive members 25 and the plurality of electrically conductive members 26 can be mechanically strong and also can be prevented from being electrically worn. Meanwhile, in a case where the plurality of electrically conductive members 25 and the plurality of electrically conductive members 26 each have an outside diameter of not more than 30 μm, the plurality of electrically conductive members 25 and the plurality of electrically conductive members 26 are bent like hair, so that the plurality of electrically conductive members 25 and the plurality of electrically conductive members 26 easily spread and easily sway.

The plurality of electrically conductive members 25 and the plurality of electrically conductive members 26 each can be a carbon fiber having an outside diameter of 7 μm, or an electrically conductive fiber made of stainless steel (SUS) and having an outside diameter of 12 µm or 25 µm.

The base end part 33 of the discharge electrode 21 has (i) a sheet metal mounting part 33a for mounting the discharge electrode 21 on the ion generating element substrate 14 and (ii) a binding part 33b for binding the plurality of electrically conductive members 25 of the tip part 31 at the connection end. As in the case of base end part 33 of the discharge electrode 21, the base end part 34 of the discharge electrode 22 has (i) a sheet metal mounting part 34a for mounting the discharge electrode 22 on the ion generating element substrate 14 and (ii) a binding part 34b for binding the plurality of electrically conductive members 26 of the tip part 32 at the connection end.

Next, a length of the tip part 31 of the discharge electrode 21 is described with reference to FIG. 3.

Figure 3:
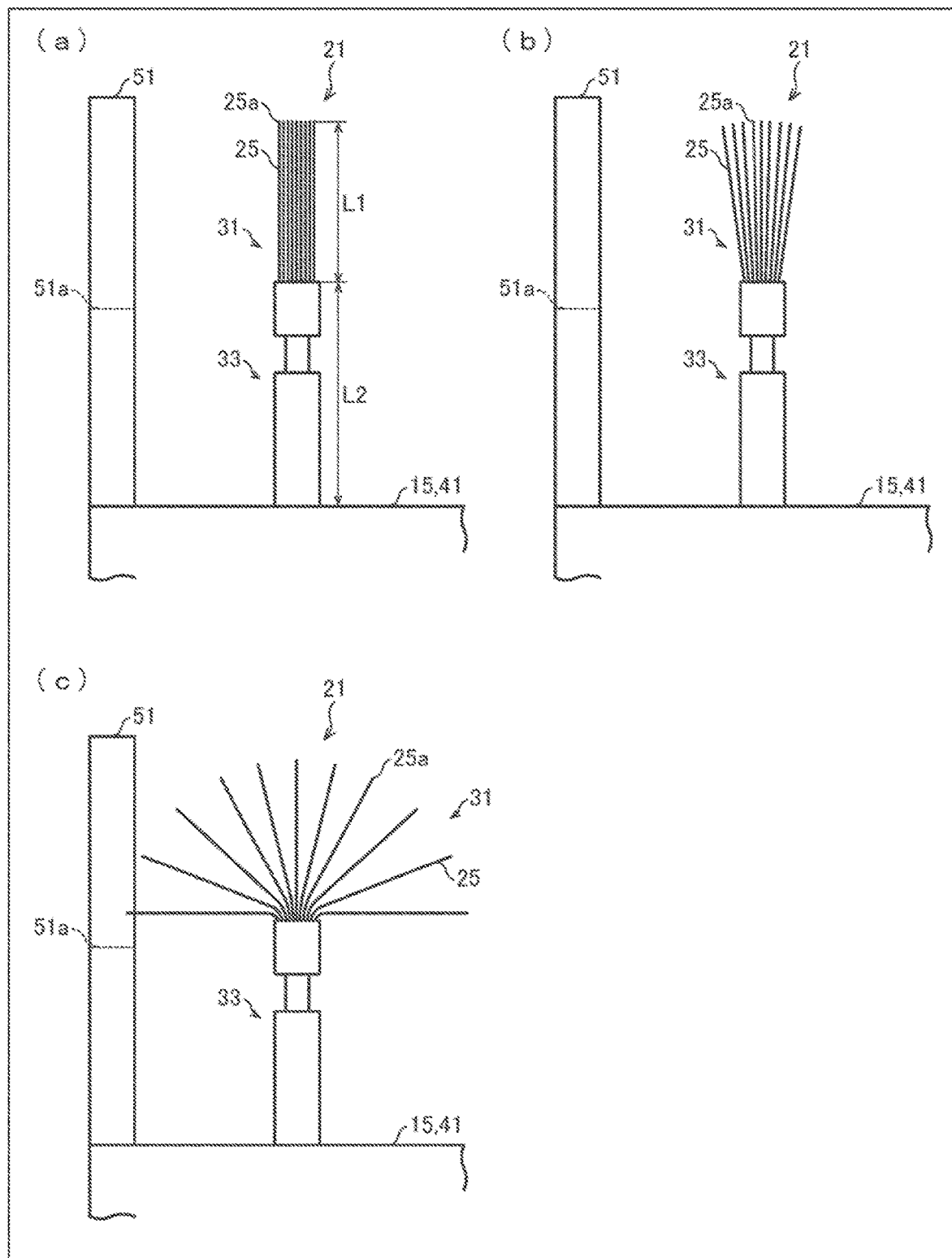
FIGS. 3a-3c are front views each schematically illustrating an arrangement of a discharge electrode and a protective plate which are illustrated in each of FIG. 1 and FIG. 2.

FIG. 3 is front views each schematically illustrating an arrangement of the discharge electrode 21 and a protective plate 51 which are illustrated in each of FIG. 1 and FIG. 2. FIG. 3 illustrates how the tip part 31 of the discharge electrode 21 changes in shape in accordance with a voltage applied to the discharge electrode 21 (and between the discharge electrode 21 and the induction electrode 23). Note that same applies to the discharge electrode 22 (not illustrated in FIG. 3).

L1 shown in FIG. 3 refers to a length of the tip part 31 of the discharge electrode 21, i.e., a length (protrusion length) for which the plurality of linear electrically conductive members 25 protrudes from the base end part 33. L2 shown in FIG. 3 refers to a length (protrusion length) for which the base end part 33 of the discharge electrode 21 protrudes (is exposed) from the lid 15, i.e., the insulating sealing member 41.

(a) of FIG. 3 illustrates a state in which no voltage is applied to the discharge electrode 21. In this case, the tips of the plurality of linear electrically conductive members 25 are closed in the tip part 31 of the discharge electrode 21.

(b) of FIG. 3 illustrates a state in which a pulse having a high voltage is being applied to the discharge electrode 21. In this case, in the tip part 31 of the discharge electrode 21, the plurality of electrically conductive members 25 electrically repel each other because the electrically conductive members 25 are homopolar. This causes the electrically conductive members 25 to be bent and consequently be shaped as if a tip of a brush was opened.

Meanwhile, at the tips of the electrically conductive members 25, positive ions are generated. As described above, the electrically conductive members 25 are shaped as if the tip of the brush was opened. This results in an increase in area of a region in which positive ions are generated. Thus, the discharge electrode 21 of Embodiment 1 causes a further increase in amount of generation of ions than a needle-like discharge electrode in a case where an identical voltage is applied to each of the discharge electrode 21 and the needle-like discharge electrode.

(c) of FIG. 3 illustrates a state in which a pulse having a higher voltage is being applied to the discharge electrode 21. In this case, in the tip part 31 of the discharge electrode 21, the plurality of electrically conductive members 25 electrically further repel each other. This causes the electrically conductive members 25 to be shaped as if the tip of the brush was further opened. Thus, ions are generated in a larger amount.

The plurality of electrically conductive members 25 of the discharge electrode 21 is electrically attracted to the induction electrode 23 whose polarity is opposite from that of the plurality of electrically conductive members 25. This may cause one or more of the plurality of electrically conductive members 25 to be greatly bent toward the induction electrode 23.

In order to overcome the above problem, Embodiment 1 causes the protrusion length L1 of the electrically conductive members 25 to be shorter than the protrusion length L2 of the base end part 33. Thus, even in a case where the electrically conductive members 25 are bent by being electrically attracted to the induction electrode 23, or in a case where the electrically conductive members 25 are bent by a dynamic force (e.g., a touch by a person) exerted thereon, the electrically conductive members 25 do not contact the insulating sealing member 41. This makes it possible to prevent, without fail, (i) a trouble such that abnormal electric discharge, an electric current leakage, or the like occurs in a part of the electrically conductive members 25 in which part the electrically conductive members 25 contact the insulating sealing member 41, so that an amount of generation of ions is reduced or becomes zero, (ii) a trouble such that the transformer drive circuit substrate 12, the high voltage transformer 13, and the ion generating element substrate 14, which are contained in the case 10, are broken by occurrence therein abnormal electric discharge, an electric current leakage, or the like, and (iii) a trouble of an increase in noise figure of the ion generating device 1.

There is a case where the case 10 is made electrostatic by the high voltage transformer 13, so that a dust or the like adheres to the surface of the lid 15 or the insulating sealing member 41. In particular, in a case where the insulating sealing member 41 is an epoxy resin, an urethane resin, or the like, a dust or the like easily adheres thereto because such an insulating sealing member 41 has a high frictional resistance. In view of this, abnormal electric discharge, an electric current leakage, or the like (described earlier) may occur. In order to overcome the above problem, Embodiment 1 makes it possible to prevent abnormal electric discharge, an electric current leakage, or the like from occurring in the part of the electrically conductive members 25 in which part the electrically conductive members 25 contact the insulating sealing member 41.

Note that the length of the tip parts 31 and 32 of the discharge electrodes 21 (the protrusion length L1 of the electrically conductive members 25 and the electrically conductive members 26) is not particularly limited provided that the length is set to be shorter than the protrusion length L2 of the base end parts 33 and 34 as described earlier. Note, however, that the tip parts 31 and 32 whose length is too short make it difficult for the electrically conductive members 25 and the electrically conductive members 26 to be bent. This causes the electrically conductive members 25 and the electrically conductive members 26 to less spread and less sway, so that an effect of the brush-like discharge electrode cannot be sufficiently obtained. The tip parts 31 and 32 which have a longer length make the ion generating device 1 larger in size. Thus, the tip parts 31 and 32 desirably have a length of not less than 3 mm. Note that the tip parts 31 and 32 can also have a length of not less than 5 mm. The protrusion length L2 of the base end parts 33 and 34 is desirably not more than 5 times longer than the length of the tip parts 31 and 32 (the protrusion length L1 of the electrically conductive members 25 and the electrically conductive members 26).

Next, the protective plates 51 and 52 are described with reference to FIG. 1 through FIG. 3.

The ion generating device 1 is not necessarily placed, during a period in which the ion generating device 1 has been produced and then is mounted in various electrical apparatuses, on a base on which to place the ion generating device 1 (hereinafter, the "base" is referred to as a "placing base", not illustrated) in such a state as illustrated in each of FIG. 1 and FIG. 2. For example, the ion generating device 1 which is placed on the placing base in such a state as illustrated in each of FIG. 1 and FIG. 2 may be turned upside down so as to be placed on the placing base. As described above, overturning of the ion generating device 1 during, for example, a production process may cause breakage (deformation) such as a break in a brush part which break is caused by a contact between (a) the discharge electrodes 21 and 22 and (b) a floor such as the placing base.

In order to overcome the above problem, Embodiment 1 is arranged such that the protective plates 51 and 52 for protecting the respective discharge electrodes 21 and 22 protrude so as to be adjacent to the respective discharge electrodes 21 and 22.

Note that according to Embodiment 1, the ion generating element substrate 14 in which the discharge electrodes 21 and 22 protrude is provided in an end of a rear part of the upper surface of the case 10, which is quadrangular.

The ion generating element substrate 14 is rectangular, and the discharge electrodes 21 and 22 are arranged in a longer side direction of the ion generating element substrate 14. The ion generating element substrate 14 has a long side 14a that (i) is a side parallel to the direction in which the discharge electrodes 21 and 22 are arranged and (ii) faces a side 10a of the rear part of the case 10 so as to be parallel to the side 10a.

In view of the above, according to Embodiment 1, on both ends of the rear part of the upper surface of the case 10, the protective plates 51 and 52 protrude so as to be adjacent to the respective discharge electrodes 21 and 22.

The protective plates 51 and 52 are juxtaposed to each other while the discharge electrodes 21 and 22 are sandwiched therebetween in the longer side direction of the ion generating element substrate 14 (i.e., a direction parallel to the long side 14a of the ion generating element substrate 14), which longer side direction is the direction in which the discharge electrodes 21 and 22 are arranged.

The protective plates 51 and 52 have a height whose maximum value is greater than a height of the discharge electrodes 21 and 22. The protective plates 51 and 52 vertically protrude, on the insulating sealing member 41 or in an upper part of the lid 15, or by being integrally molded with the lid 15, so as to further protrude from the surface of the ion generating element substrate 14 than the tip parts 31 and 32 of the discharge electrodes 21 and 22.

With the arrangement, even in a case where the ion generating device 1 is, for example, overturned, the discharge electrodes 21 and 22 can be prevented from directly contacting an object, provided on an outside of the ion generating device 1, such as the placing base, so that the discharge electrodes 21 and 22 can be prevented from, for example, being broken by the contact.

Note here that the height of the protective plates 51 and 52 refers to a vertical length, i.e., a height from the surface of the insulating sealing member 41 to an upper surface of the protective plate 51 as well as a height from the surface of the insulating sealing member 41 to an upper surface of the protective plate 52.

The height of the protective plates 51 and 52 is not particularly limited provided that the protective plates 51 and 52 further protrude from the surface of the ion generating element substrate 14 than the tip parts 31 and 32 of the discharge electrodes 21 and 22.

Note, however, that the protective plates 51 and 52 which have a greater height make the ion generating device 1 larger in size accordingly. Thus, the protective plates 51 and 52 desirably have a height that is great enough for the discharge electrodes 21 and 22 to be prevented from directly contacting the object, provided on the outside of the ion generating device 1, such as the placing base in a case where the ion generating device 1 is, for example, overturned. For example, the height from the surface of the insulating sealing member 41 to the upper surfaces of the protective plates 51 and 52 is desirably slightly greater than a height from the surface of the insulating sealing member 41 to tips of the tip parts 31 and 32 (i.e., a maximum value of a height from the surface of the insulating sealing member 41 to the tips 25a and 26a of the electrically conductive members 25 and the electrically conductive members 26) in the discharge electrodes 21 and 22.

The protective plates 51 and 52 are spaced from the respective discharge electrodes 21 and 22 so that a distance between the discharge electrode 21 and the protective plate 51 and a distance between the discharge electrode 22 and the protective plate 52 are each longer than the length of the tip parts 31 and 32 of the discharge electrodes 21 and 22.

Thus, as illustrated in (b) and (c) of FIG. 3, even in a case where the electrically conductive members 25 or the electrically conductive members 26 repel each other and the tip part 31 or 32 spreads, so that the electrically conductive members 25 or the electrically conductive members 26 lean at any angle, the electrically conductive members 25 and the electrically conductive members 26 do not directly contact the respective protective plates 51 and 52. This makes it possible to prevent occurrence of a leakage.

When the discharge electrodes 21 and 22 are seen through the respective protective plates 51 and 52 (i.e., when the ion generating device 1 is seen from a direction parallel to the side 10a of the case 10), respective parts of the protective plates 51 and 52 which parts face the respective tip parts 31 and 32 of the discharge electrodes 21 and 22 are each formed in a shape of a notched plate. Thus, the protective plate 51 is provided with an opening 51a, facing the discharge electrode 21, for exposing the tip part 31. Meanwhile, the protective plate 52 is provided with an opening 52a, facing the discharge electrode 22, for exposing the tip part 32.

The protective plates 51 and 52, which are thus provided with the respective openings 51a and 52a, do not inhibit the discharge electrodes 21 and 22 from releasing ions, so that the ions can be satisfactorily released.

According to Embodiment 1, the mounting parts 33a and 34a, which are plate-like, are mounted on the ion generating element substrate 14 so that a direction normal to plate surfaces of the mounting parts 33a and 34a is a front and rear direction. It is easy for the electrically conductive members 25 and the electrically conductive members 26 to lean in a direction in which the sheet metal mounting parts 33a and 34a have a small thickness, whereas it is difficult for the electrically conductive members 25 and the electrically conductive members 26 to lean in a direction in which the sheet metal mounting parts 33a and 34a have a great thickness. Thus, it is easy for the discharge electrodes 21 and 22 to lean in the front and rear direction, whereas it is difficult for the discharge electrodes 21 and 22 to lean in a right and left direction. This prevents the protective plates 51 and 52, which are provided in the right and left direction of the discharge electrodes 21 and 22, from being in proximity to the electrically conductive members 25 and the electrically conductive members 26 of the discharge electrodes 21 and 22, so that a leakage can be effectively prevented.

In other words, the plate-like mounting parts 33a and 34a of the discharge electrodes 21 and 22 are desirably mounted on the ion generating element substrate 14 so that the protective plates 51 and 52 are absent in the direction normal to the plate surfaces of the mounting parts 33a and 34a.

(Variation)

The description of Embodiment 1 takes, as an example, a case where the protective plates 51 and 52 are juxtaposed to each other while the discharge electrodes 21 and 22 are sandwiched therebetween in the longer side direction of the ion generating element substrate 14. Note, however, that Embodiment 1 is not limited to this.

It is possible to provide only one protective plate provided that the protective plate is provided at a location and a height that allow the electrically conductive members 25 and the electrically conductive members 26 to be prevented from directly contacting the object, provided on the outside of the ion generating device 1, even in a case where the ion generating device 1 is, for example, overturned.

The description of Embodiment 1 also takes, as an example, a case where the ion generating element substrate 14 is provided in the rear part of the case 10. Note, however, that the ion generating element substrate 14 can also be provided in the front part or a central part of the case 10.

Note that positive ions and negative ions can be generated by the discharge electrodes 21 and 22 even in a case where the induction electrodes 23 and 24, which are used in Embodiment 1, are not used. Note, however, that use of the induction electrodes 23 and 24 is desirable. This is because use of the induction electrodes 23 and 24 causes a further increase in (i) electric field intensity of the discharge electrodes 21 and 22 and (ii) amount of generation of ions than non-use of the induction electrodes 23 and 24.

Embodiment 2

Another embodiment of the present invention is described with reference to FIG. 4 and FIG. 5. Note that Embodiment 2 describes points of difference from Embodiment 1.

Figure 4:
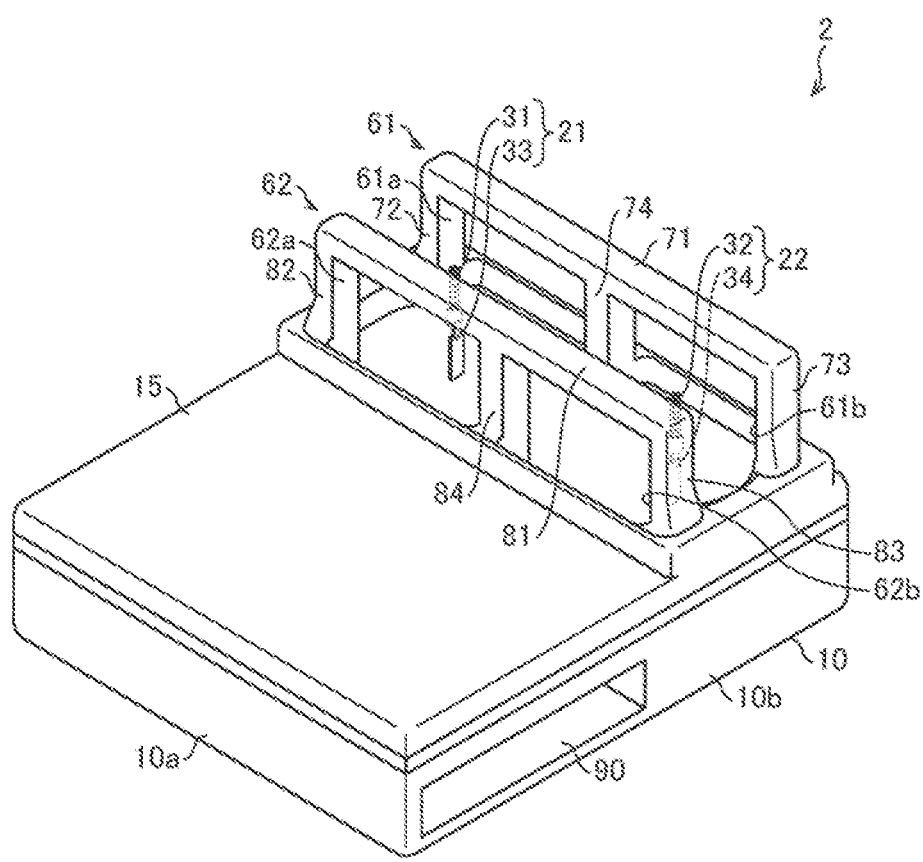
FIG. 4 is a perspective view schematically illustrating an arrangement of an ion generating device in accordance with Embodiment 2 of the present invention.

FIG. 4 is a perspective view schematically illustrating an arrangement of an ion generating device in accordance with Embodiment 2. FIG. 5 is a front view, a plan view, and a side view each schematically illustrating the arrangement of the ion generating device.

An ion generating device 2 in accordance with Embodiment 2 is arranged as in the case of the ion generating device 1 in accordance with Embodiment 1 except (i) that in Embodiment 2, protective plates 61 and 62 (protruding members) for protecting discharge electrodes 21 and 22, instead of the protective plates 51 and 52, are juxtaposed to each other while the discharge electrodes 21 and 22 are sandwiched therebetween in a shorter side direction of an ion generating element substrate 14 (i.e., a direction parallel to a short side 14b of the ion generating element substrate 14), which shorter side direction is perpendicular to a direction in which the discharge electrodes 21 and 22 are arranged, and mounting parts 33a and 34a of the discharge electrodes 21 and 22 tend to lean in a direction different from a direction in which the mounting parts 33a and 34a of Embodiment 1 tend to lean and (ii) that in Embodiment 2, a case 10 has a side surface provided with a recess 90 instead of the external connection substrate 11, and the recess 90 is provided with a plurality of connection terminals 91.

The protective plates 61 and 62 have a height whose maximum value is greater than a height of the discharge electrodes 21 and 22. The protective plates 61 and 62 vertically protrude, on an insulating sealing member 41 or in an upper part of a lid 15, or by being integrally molded with the lid 15, so as to further protrude from a surface of the ion generating element substrate 14 than tip parts 31 and 32 of the discharge electrodes 21 and 22.

With the arrangement, also according to Embodiment 2, even in a case where the ion generating device 2 is, for example, overturned, the discharge electrodes 21 and 22 can be prevented from directly contacting an object, provided on an outside of the ion generating device 2, such as a placing base, so that the discharge electrodes 21 and 22 can be prevented from, for example, being broken by the contact.

Note here that the height of the protective plates 61 and 62 refers to a vertical length, i.e., a height from a surface of the insulating sealing member 41 to an upper surface of the protective plate 61 as well as a height from the surface of the insulating sealing member 41 to an upper surface of the protective plate 62. Note also that the upper surfaces of the protective plates 61 and 62 specifically refer to upper surfaces of beam parts 71 and 81 (described later).

Also according to Embodiment 2, the height of the protective plates 61 and 62 is not particularly limited as in the case of the protective plates 51 and 52 provided that the protective plates 61 and 62 further protrude from the surface of the ion generating element substrate 14 than the tip parts 31 and 32 of the discharge electrodes 21 and 22.

Note, however, that the protective plates 61 and 62 which have a greater height make the ion generating device 2 larger in size accordingly. Thus, the protective plates 61 and 62 desirably have a height that is great enough for the discharge electrodes 21 and 22 to be prevented from directly contacting the object, provided on the outside of the ion generating device 2, such as the placing base in a case where the ion generating device 2 is, for example, overturned. For example, the height from the surface of the insulating sealing member 41 to the upper surfaces of the protective plates 61 and 62 is desirably slightly greater than a height from the surface of the insulating sealing member 41 to tips of the tip parts 31 and 32 (i.e., a maximum value of a height from the surface of the insulating sealing member 41 to tips 25a and 26a of electrically conductive members 25 and electrically conductive members 26) in the discharge electrodes 21 and 22.

In order that a distance between (a) the discharge electrode 21 or the discharge electrode 22 and (b) the protective plate 61 or the protective plate 62 is longer than a length of the tip parts 31 and 32 of the discharge electrodes 21 and 22, the protective plates 61 and 62 are provided so as to face each other while being spaced from each other.

Specifically, the protective plates 61 and 62 are adjacent to each other so that a distance therebetween is not less than two times longer than the length of the tip parts 31 and 32 of the discharge electrodes 21 and 22. Thus, also according to Embodiment 2, even in a case where the electrically conductive members 25 or the electrically conductive members 26 repel each other and the tip part 31 or 32 spreads, so that the electrically conductive members 25 or the electrically conductive members 26 lean at any angle, the electrically conductive members 25 and the electrically conductive members 26 do not directly contact the protective plates 61 and 62. This makes it possible to prevent occurrence of a leakage.

Figure 5:
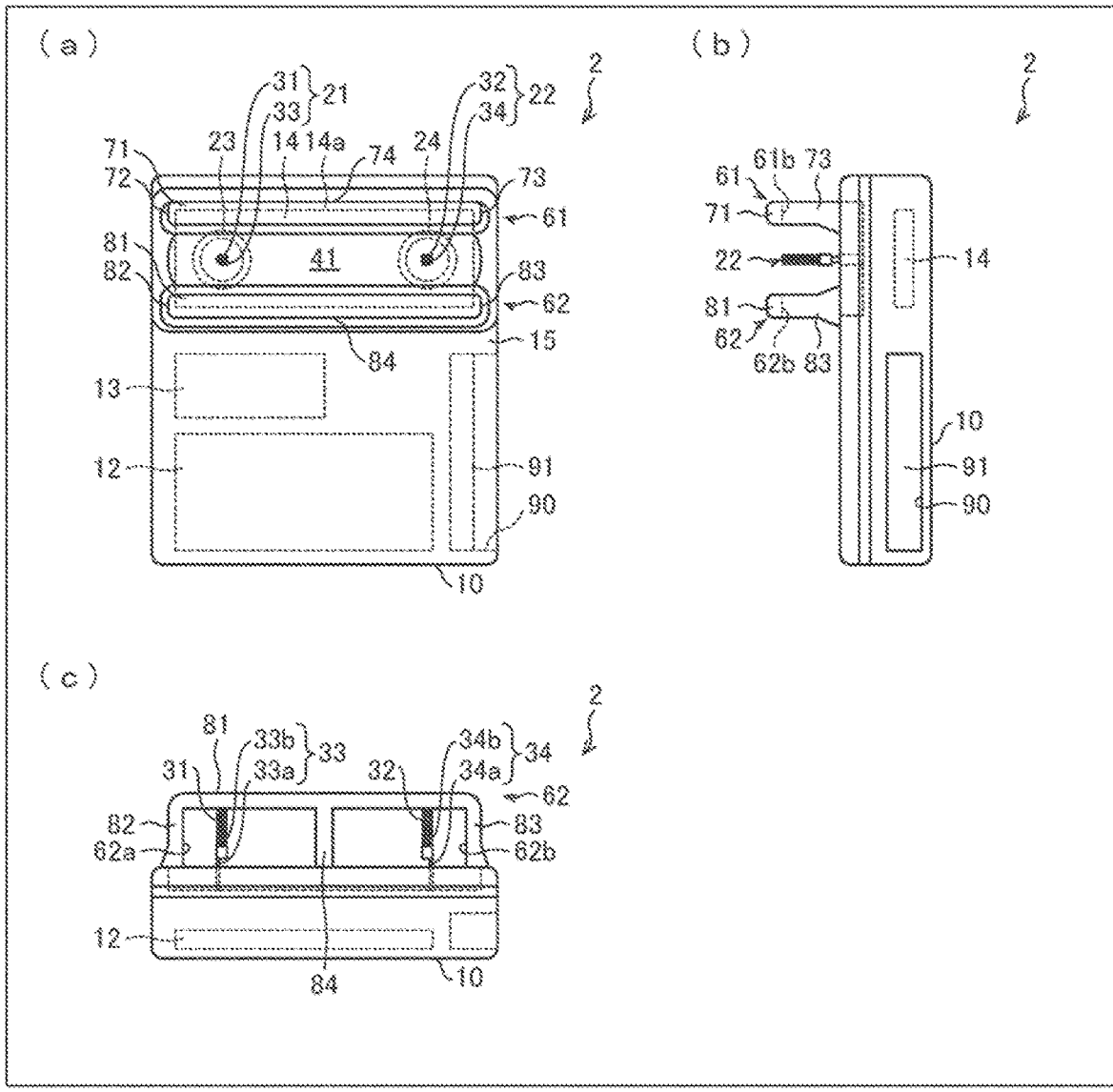
FIGS. 5a-5c are, respectively, a plan view, a side view, and a front view each schematically illustrating the arrangement of the ion generating device in accordance with Embodiment 2 of the present invention.

For example, the tip parts 31 and 32 illustrated in each of FIG. 4 and FIG. 5 may decrease in amount of electric discharge due to adhesion of, for example, a dust to the electrically conductive members 25 and the electrically conductive members 26 which adhesion is caused by static electricity generated by electric discharge. Thus, there is a case where the ion generating device 2 which is provided in an electrical apparatus is removed by a user so that cleaning is carried out for removing, for example, a dust from the electrically conductive members 25 and the electrically conductive members 26 of the tip parts 31 and 32. Note here that an upper limit of the distance between the protective plates 61 and 62 is not particularly limited provided that the distance is not less than two times longer than the length of the tip parts 31 and 32 of the discharge electrodes 21 and 22. Note, however, that the distance between the protective plates 61 and 62 is desirably set at a distance that prevents a finger of the user from touching the electrically conductive members 25 and the electrically conductive members 26 of the tip parts 31 and 32. This makes it possible to prevent a finger of the user from touching the electrically conductive members 25 and the electrically conductive members 26 of the tip parts 31 and 32.

The protective plates 61 and 62 are each formed like glasses. Specifically, the protective plate 61 has a beam part 71 that is made of a horizontally long plate parallel to the surface of the ion generating element substrate 14, support parts 72 and 73 that are supports for supporting both ends of the beam part 71, and a support part 74 that is a support for supporting a central part of the beam part 71.

A space between the support parts 72 and 74, which are adjacent to each other, and a space between the support parts 74 and 73, which are adjacent to each other, are opened. Thus, the protective plate 61 is provided with two openings 61a and 61b.

As in the case of the protective plate 61, the protective plate 62 has a beam part 81 that is made of a horizontally long plate parallel to the surface of the ion generating element substrate 14, support parts 82 and 83 that are supports for supporting both ends of the beam part 81, and a support part 84 that is a support for supporting a central part of the beam part 81.

A space between the support parts 82 and 84, which are adjacent to each other, and a space between the support parts 84 and 83, which are adjacent to each other, are opened. Thus, the protective plate 62 is provided with two openings 62a and 62b.

The support parts 72 and 73 protrude at both ends of the ion generating element substrate 14 in a longer side direction of the ion generating element substrate 14 so as to face each other. The support part 74 protrudes in a central part of the ion generating element substrate 14 in the longer side direction of the ion generating element substrate 14 so as to face each of the support parts 72 and 73.

As in the case of the support parts 72 and 73, the support parts 82 and 83 protrude at both ends of the ion generating element substrate 14 in a longer side direction of the ion generating element substrate 14 so as to face each other. The support part 84 protrudes in a central part of the ion generating element substrate 14 in the longer side direction of the ion generating element substrate 14 so as to face each of the support parts 82 and 83.

With the arrangement, the beam parts 71 and 81 are each provided so as to be parallel to a long side 14a of the ion generating element substrate 14 and serve as a bridge to connect one end to the other end of the ion generating element substrate 14 in the longer side direction of the ion generating element substrate 14.

When the discharge electrodes 21 and 22 are seen through protective plates 61 and 62 (i.e., when the ion generating device 2 is seen from a direction parallel to a side 10a of the case 10), the discharge electrode 21 is seen through the openings 62a and 61b, and the discharge electrode 22 is seen through the openings 62b and 61a.

These openings 61a, 61b, 62a, and 62b each function as a ventilation hole through which to cause gas, by which ions generated by the discharge electrodes 21 and 22 of the ion generating device 2 are carried, to pass.

According to the examples shown in FIG. 4 and FIG. 5, the protective plates 61 and 62 are provided at a height that causes the tips of the tip parts 31 and 32 of the discharge electrodes 21 and 22 (i.e., the tips of the electrically conductive members 25 and the electrically conductive members 26) to be hidden by the beam parts 71 and 81.

Note, however, that the height of the protective plates 61 and 62 (i.e., a height from the surface of the insulating sealing member 41 to upper surfaces of the beam parts 71 and 81) only needs to be set at a height greater than the height from the surface of the insulating sealing member 41 to the tips 25a and 26a of the electrically conductive members 25 and the electrically conductive members 26. The protective plates 61 and 62 can also be provided at a height that allows an entirety of the discharge electrode 21 to be seen through the openings 62a and 61b and allows an entirety of the discharge electrode 22 to be seen through the openings 62b and 61a.

According to Embodiment 2, as described earlier, since at least a part of the discharge electrode 21 is seen through the openings 62a and 61b and at least a part of the discharge electrode 22 is seen through the openings 62b and 61a, the protective plates 61 and 62 do not inhibit the discharge electrodes 21 and 22 from releasing ions, so that the ions can be satisfactorily released.

According to Embodiment 2, the mounting parts 33a and 34a, which are plate-like, are mounted on the ion generating element substrate 14 so that a direction normal to plate surfaces of the mounting parts 33a and 34a is a right and left direction. As described earlier, it is easy for the electrically conductive members 25 and the electrically conductive members 26 to lean in a direction in which the mounting parts 33a and 34a, which are sheet metal, have a small thickness, whereas it is difficult for the electrically conductive members 25 and the electrically conductive members 26 to lean in a direction in which the mounting parts 33a and 34a, which are sheet metal, have a great thickness. Thus, it is easy for the discharge electrodes 21 and 22 to lean in the right and left direction, whereas it is difficult for the discharge electrodes 21 and 22 to lean in a front and rear direction. This prevents the protective plates 61 and 62, which are provided in the front and rear direction of the discharge electrodes 21 and 22, from being in proximity to the electrically conductive members 25 and the electrically conductive members 26 of the discharge electrodes 21 and 22, so that a leakage can be effectively prevented.

In other words, the plate-like mounting parts 33a and 34a of the discharge electrodes 21 and 22 are desirably mounted on the ion generating element substrate 14 so that the protective plates 61 and 62 are absent in the direction normal to the plate surfaces of the mounting parts 33a and 34a.

Thus, in a case where the protective plates 61 and 62 are provided so as to be adjacent to the discharge electrodes 21 and 22 in the direction parallel to the short side 14b of the ion generating element substrate 14 as illustrated in FIG. 4 and FIG. 5, the protective plates 61 and 62 are not in proximity to the electrically conductive members 25 and the electrically conductive members 26, so that a leakage can be effectively prevented.

It is a matter of course that Embodiment 2 can also be varied as in the case of Embodiment 1, though a description of a variation of Embodiment 2 is omitted.

Embodiment 3

A further embodiment of the present invention is described with reference to FIG. 6. Embodiment 3 describes an electrical apparatus including an ion generating device.

Figure 6:
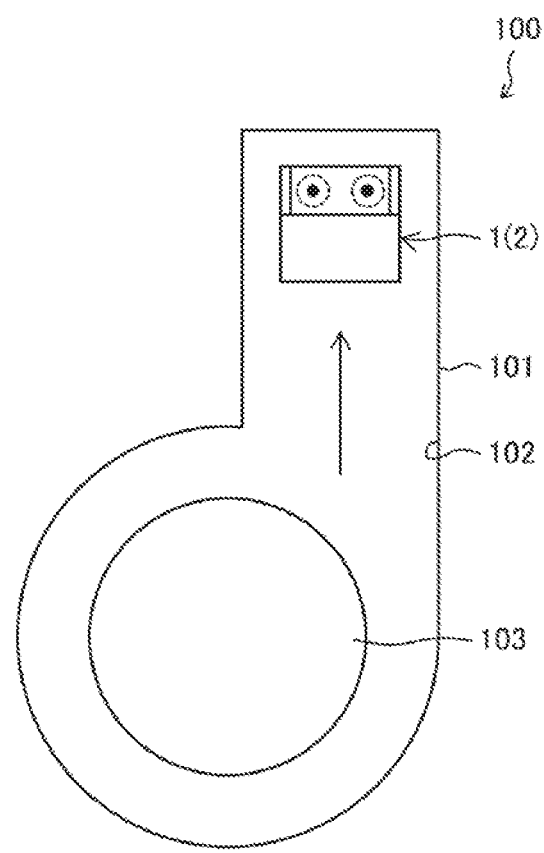
FIG. 6 is a plan view showing an example of an arrangement of an inside of an electrical apparatus in accordance with Embodiment 3 of the present invention.

FIG. 6 is a plan view showing an example of an arrangement of an inside of an electrical apparatus in accordance with Embodiment 3.

The following description takes, as an example, a case where an ion generating device 1 is used as the ion generating device. Note, however, that instead of the case where the ion generating device 1 is used as the ion generating device, a case where an ion generating device 2 is used as the ion generating device can also be taken as the example.

FIG. 6 shows an example of an electrical apparatus 100 having a casing 101 for a fan (hereinafter referred to as a "fan casing 101") part of which is provided with the ion generating device 1, the fan casing 101 constituting an air flow path 102, which is a path through which to guide, to an outside of the ion generating device 1, ions generated by the ion generating device 1.

Thus, in the air flow path 102, the ion generating device 1 and an air sending device 103 for sending gas, by which the ions generated by the ion generating device 1 are carried, are provided. The ion generating device 1 is provided on a downstream side of a direction in which the air sending device 103 sends air.

The air sending device 103 can be a sirocco fan, a crossflow fan, or another fan.

The ion generating device 1 can be integrally incorporated into the electrical apparatus 100 or can be provided so as to be detachable and attachable with respect to the electrical apparatus 100. The ion generating device 1 which is provided so as to be detachable and attachable with respect to the electrical apparatus 100 allows the ion generating device 1 to be replaced and cleaned. This facilitates maintenance of the electrical apparatus 100.

The electrical apparatus 100 is not particularly limited and can be, for example, an ion generator, an air conditioner, a dehumidification machine, a humidifier, an air cleaner, a fan heater, or another apparatus. The electrical apparatus 100 can be an electrical apparatus for use in a house or an electrical apparatus for automotive use. The electrical apparatus 100 is suitably used to condition air in, for example, a house, a room of a building, a hospital room, a vehicle, an airplane, or a vessel.

(Variation)

The description of Embodiment 3 takes, as an example, a case where the electrical apparatus 100 includes the air sending device 103. Note, however, that the air sending device 103 is dispensable. For example, the ions generated by the ion generating device 1 can also be released to the outside of the electrical apparatus 100 by, for example, thermal convection.

[Recap]

An ion generating device (1,2) in accordance with Aspect 1 of the present invention includes: a discharge electrode (21,22), protruding from a surface of the ion generating device, for generating ions by electric discharge, the discharge electrode having (i) a tip part (31,32) including a plurality of linear electrically conductive members (25,26) and (ii) a base end part (33,34) to which the plurality of electrically conductive members is attached, and the base end part protruding from the surface for a length that is longer than a length of the tip part.

With the arrangement, even in a case where the plurality of electrically conductive members is bent by a certain force exerted thereon, the plurality of electrically conductive members does not reach the surface of the ion generating device. This makes it possible to prevent the plurality of electrically conductive members from contacting the surface of the ion generating device. As a result, it is possible to prevent a decrease in amount of generation of ions which decrease is caused in a case where abnormal electric discharge, an electric current leakage, or the like is caused in the surface of the ion generating device by the plurality of electrically conductive members.

Note that the linear electrically conductive members can be, for example, straight, curved, thready, fibrous, or wiry. Examples of the "certain force" include, for example, a dynamic force (e.g., a touch by a person) and an electric force that is applied by the plurality of electrically conductive members to the induction electrode so that the plurality of electrically conductive members stably carries out electric discharge during the electric discharge.

From the viewpoint that the ion generating device is made smaller in size as much as possible, a high voltage circuit is to be provided in the ion generating device, and the plurality of electrically conductive members is provided above the surface of the ion generating device. In view of this, in Aspect 2 of the present invention, the ion generating device can be arranged in Aspect 1 of the present invention to further include: a high voltage circuit (high voltage transformer 13), provided thereinside, for applying a high voltage to the discharge electrode. As in the case of the ion generating device in accordance with Aspect 1 of the present invention, the ion generating device in accordance with Aspect 2 of the present invention makes it possible to (i) prevent the plurality of electrically conductive members from causing abnormal electric discharge, an electric current leakage, or the like in the surface of the ion generating device and (ii) prevent the surface and the high voltage circuit from being broken by occurrence of abnormal electric discharge in the high voltage circuit.

In Aspect 3 of the present invention, the ion generating device can be arranged in Aspect 1 or 2 of the present invention to further include: an induction electrode (23,24), provided thereinside, for generating ions between the induction electrode and the discharge electrode. In a case where the induction electrode is provided, the discharge electrode has a higher electric field intensity, so that the ions can be generated in a larger amount, or a lower voltage can be applied to the discharge electrode. Further, as in the case of the ion generating device in accordance with Aspect 1 or 2 of the present invention, the ion generating device in accordance with Aspect 3 of the present invention makes it possible to (i) prevent the plurality of electrically conductive members from causing abnormal electric discharge, an electric current leakage, or the like in the surface of the ion generating device and (ii) prevent the surface from being broken.

Note that an electrical apparatus (100) including an ion generating device having the above arrangement can yield an effect similar to those described above.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

REFERENCE SIGNS LIST 1,2 Ion generating device
10 Case
10a Side
11 External connection substrate
12 Transformer drive circuit substrate
13 High voltage transformer (high voltage circuit)
14 Ion generating element substrate (substrate)
14a Long side
14b Short side
15 Lid
16 Connection terminal
21,22 Discharge electrode
23,24 Induction electrode
25,26 Electrically conductive member
25a,26a Tip
31,32 Tip part
33,34 Base end part
33a,34a Mounting part
33b,34b Binding part
41 Insulating sealing member
51,52,61,62 Protective plate (protruding member)
51a,52a,61a,61b,62a,62b Opening 71,81 Beam part
72,73,74,82,83,84 Support part
90 Recess
91 Connection terminal
100 Electrical apparatus
101 Fan casing
102 Air flow path
103 Air sending device

The invention claimed is:

1. An ion generating device comprising:
a discharge electrode, protruding from a surface of the ion generating device, for generating ions by electric discharge,
the discharge electrode having (i) a tip part including a plurality of linear electrically conductive members and (ii) a base end part to which the plurality of electrically conductive members is attached, and
the base end part protruding from the surface for a length that is longer than a length of the tip part,
the ion generating device further comprising one or more protruding members vertically protrude from the surface,
wherein a distance between a connection end of the tip part of the discharge electrode and the protruding members is longer than the length of the tip part.

2. The ion generating device as set forth in claim 1, further comprising:
a high voltage circuit, provided thereinside, for applying a high voltage to the discharge electrode.

3. The ion generating device as set forth in claim 1, further comprising:
an induction electrode, provided thereinside, for generating ions between the induction electrode and the discharge electrode.

4. An electrical apparatus comprising:
an ion generating device recited in claim 1.

5. The ion generating device of claim 1, wherein the one or more protruding members having an opening so as to expose the tip part.

6. The ion generating device of claim 5, wherein the opening is formed as a u-shaped notch on each of the one or more protruding members.

7. The ion generating device of claim 5, wherein the opening is a hole formed on each of the one or more protruding members.

* * * * *